(12) United States Patent
Burdumy

(10) Patent No.: US 7,963,286 B2
(45) Date of Patent: Jun. 21, 2011

(54) COMBINATION BITE BLOCK, TONGUE DEPRESSOR/RETRACTOR AND AIRWAY

(75) Inventor: Theodore James Burdumy, Santa Maria, CA (US)

(73) Assignee: InfoHealthNetwork, Inc., Santa Maria, CA (US)

( * ) Notice: Subject to any disclaimer, the term of this patent is extended or adjusted under 35 U.S.C. 154(b) by 183 days.

(21) Appl. No.: 12/186,356

(22) Filed: Aug. 5, 2008

(65) Prior Publication Data

US 2009/0050161 A1    Feb. 26, 2009

Related U.S. Application Data

(60) Provisional application No. 60/955,287, filed on Aug. 10, 2007, provisional application No. 60/956,418, filed on Aug. 17, 2007.

(51) Int. Cl.
*A61C 5/14* (2006.01)
*A61C 3/00* (2006.01)
*A61C 5/00* (2006.01)

(52) U.S. Cl. .............................. 128/861; 433/6; 433/140

(58) Field of Classification Search ........... 128/859–862, 128/848; 602/902; 600/240, 235, 237, 238, 600/239; 433/6, 140, 148, 149, 136, 138
See application file for complete search history.

(56) References Cited

U.S. PATENT DOCUMENTS

| 4,270,529 | A | 6/1981 | Muto |
| 4,351,331 | A | 9/1982 | Gereg |
| 4,425,911 | A | 1/1984 | Luomanen et al. |
| 4,495,945 | A | 1/1985 | Liegner |
| D283,158 | S | 3/1986 | Jackson |
| 4,640,273 | A | 2/1987 | Greene et al. |
| 5,009,227 | A | 4/1991 | Nieuwstad |
| D329,901 | S | 9/1992 | Jackson |
| 5,174,284 | A | 12/1992 | Jackson |

(Continued)

FOREIGN PATENT DOCUMENTS

GB        2432767 A  *  5/2007

(Continued)

OTHER PUBLICATIONS

Tod F. Tolan et al, "Dental Injuries in Anesthesia: Incidence and Preventive Strategies", American Society of Anesthesiologists, Annual Meeting Abstracts, Oct. 12-22, 2008 Orlando, Florida.

*Primary Examiner* — Patricia M Bianco
*Assistant Examiner* — Ophelia Hawthorne
(74) *Attorney, Agent, or Firm* — Fish & Associates, PC

(57) ABSTRACT

A combination bite block, tongue depressor/retractor and airway for establishing and maintaining an open airway while preventing emergence clenching and the resulting dental and soft tissue damage associated with emergence clenching in procedures where anesthesia and/or sedation are used, or when the patient is not in control of their own airway, regardless of the cause. The inventive subject matter includes a tongue depressor/retractor component in both right and left conformations; and a bite block component. The bite block component is a wedge shaped, compressible component that is inserted between the upper and lower molars on either the right or left side of the mouth. The tongue depressor component is comprised by a flat portion of that is inserted into the side of the bite block, and an optional curved portion that retracts the tongue off of the posterior pharynx when in place.

11 Claims, 9 Drawing Sheets

U.S. PATENT DOCUMENTS

| | | |
|---|---|---|
| 5,305,742 A | 4/1994 | Styers et al. |
| D348,932 S | 7/1994 | Jackson |
| 5,413,095 A | 5/1995 | Weaver |
| D399,950 S | 10/1998 | Shepard |
| 5,855,535 A * | 1/1999 | Shafer ............................. 482/11 |
| 6,257,238 B1 | 7/2001 | Meah |
| 6,652,276 B2 * | 11/2003 | Fischer et al. ................ 433/140 |
| 6,716,029 B2 | 4/2004 | Fischer et al. |
| 6,908,308 B2 * | 6/2005 | Hirsch et al. .................... 433/93 |
| 2007/0015113 A1 | 1/2007 | Lavi et al. |
| 2007/0089754 A1 * | 4/2007 | Jones ............................ 128/861 |

FOREIGN PATENT DOCUMENTS

WO 2007/060388 5/2007

* cited by examiner

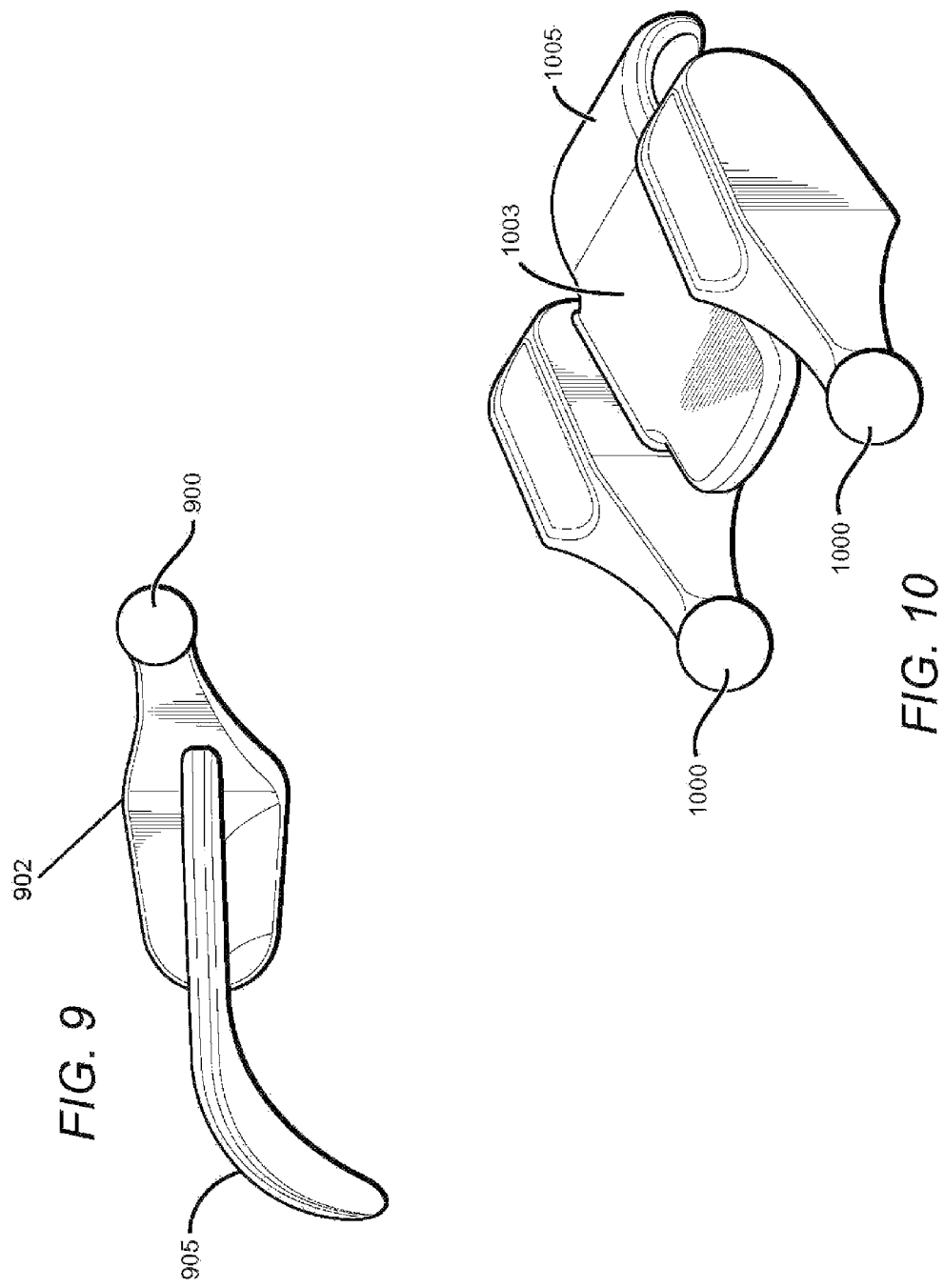

COMBINATION BITE BLOCK, TONGUE DEPRESSOR/RETRACTOR AND AIRWAY

This application claims priority to U.S. provisional application 60/955,287 and 60/956,418 filed Aug. 10, 2007 and Aug. 17, 2007 respectively, referenced herein in its entirety.

FIELD OF THE INVENTION

The field of the invention is airways and bite blocks.

BACKGROUND

About 1 in 7000 patients awakening from anesthesia experience dental injuries known as "Emergence Clenching Dental Trauma." This is reportedly the most common cause of malpractice claims against anesthesia providers.

According to the American Society of Anesthesiologists, the problem is that "Placement of an airway device (oropharyngeal airway, Laryngeal Mask Airway, Endotracheal Tube) transfers jaw clenching forces forward to two or more incisors." This is problematic because, although healthy molars and premolars tolerate vertical forces of 100-200 lb. in most patients, anterior teeth tolerate vertical forces of only 25-35 lb. and horizontal forces of less than 25 lb. Diseased or restored teeth are particularly vulnerable to injury.

The conventional solution is to "transfer clenching pressures backward and distribute the forces among the more tolerant molar teeth" using a combination airway/bite block. Commonly used airway/bite blocks include the Guedel oropharyngeal airway, the Cobe oropharyngeal airway, Williams airway intubator, Patil oral airway, Ovassapian fiberoptic intubating airway, modified Connell airway, Mehta's cuffed oropharyngeal airway, other cuffed oropharyngeal airways, the bite blocks for use in dentistry and for use in conjunction with laryngeal mask airways and endotracheal tubes. Additional examples of attempts to address the issues described above include those patents listed below. These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

| Patent No. | Issued Date | Inventor |
| --- | --- | --- |
| 4,270,529 | June 1981 | Muto |
| 4,351,331 | September 1982 | Gereg |
| 4,425,911 | January 1984 | Luomanen |
| 4,495,945 | January 1985 | Liegner |
| D283,158 | March 1986 | Jackson |
| 4,640,273 | February 1987 | Greene et al. |
| 5,009,227 | April 1991 | Nieuwstad |
| D329,901 | September 1992 | Jackson |
| 5,174,284 | December 1992 | Jackson |
| 5,305,742 | April 1994 | Styers et at. |
| D348,932 | July 1994 | Jackson |
| 5,413,095 | May 1995 | Weaver |
| D399,950 | October 1998 | Shepard |
| 6,257,238 | July 2001 | Meah |

Conventional oropharyngeal airways and combination airway/bite blocks generally suffer from significant defects. Perhaps the most significant problem is that they test to be symmetric about the midline, where the teeth are far more susceptible to damage from "emergence clenching." Other problems include: interference with tongue retraction necessary to maintain an open airway; interference with bag-mask ventilation, which may be a necessary rescue effort on induction and/or emergence from anesthesia and sedation; excessive jaw opening beyond the comfort range of many patients; a presence of acute angles that increase the risk of soft tissue damage; and lack of disposability.

What are still needed are systems, methods and devices that satisfactorily maintain an open airway while preventing emergence clenching.

SUMMARY OF THE INVENTION

The present inventive subject matter provides systems, methods and devices in which a bite block is coupled to, or includes, a tongue depressor/retractor component.

In preferred embodiments, the bite block component is wedge shaped, and is formed using a compressible material. The component is inserted between the upper and lower molars on the right side, on the left side, or on both sides of the mouth. The tongue depressor component is generally ramp-shaped, with an anterior flatter portion that is inserted into the side of the bite block, and an optional posterior curved portion that retracts the tongue off of the posterior pharynx when in place. Preferably, the tongue depressing portion is inserted into a medial slot in the bite block and the anterior portion is shortened and rounded to prevent the front teeth from contacting the tongue depressing portion. It is contemplated that the bite block component could be used with or without the tongue depressor component. Also, an embodiment is contemplated with the posterior portion of the tongue depressor shortened to facilitate endoscopic procedures when the gag reflex may still be intact.

Both right and left conformations are contemplated, as well as a bilateral conformation and different sizes to accommodate different sized patients. A single molar receiving portion with both left and right slots could be used in conjunction with either side of a tongue depressor so that it can be used in either the right or left side of the mouth. The molar receiving portion could also be permanently coupled with the tongue depressing portion or be molded from a single unit to be used in only one side of the mouth.

Embodiments can advantageously be utilized in facilitating visualization during endoscopic procedures of the airway, larynx, lungs, and gastrointestinal tract. Other contemplated uses include facilitating assisted or controlled ventilation while using a bag-mask apparatus or anesthesia machine breathing circuit via a mask, with or without additional methods of securing the airway, such as endotracheal tubes and laryngeal mask airways. To that end, a point of attachment can advantageously secure laryngeal mask airways and endotracheal tubes.

Bite block, tongue depressor/retractor and airway combinations can be used by anesthesia providers, gastroenterologists, pulmonologists, intensivists, and emergency personnel, including EMTS, Emergency Room Physicians, Emergency Room Nurses, and other first responders to medical emergencies for airway protection and maintenance as indicated by medical conditions including respiratory failure, respiratory compromise, respiratory arrest, and seizures. Additional uses include prevention of dental damage during Electroconvulsive Therapy treatment, airway management during surgical and non-surgical procedures, gastroscopy, bronchoscopy, and, in general, in any other circumstances where dental damage can occur from excess dental clenching.

Various objects, features, aspects and advantages of the inventive subject matter will become more apparent from the following detailed description of preferred embodiments,

BRIEF DESCRIPTION OF THE DRAWINGS

FIG. 9 is an embodiment of a left-seated combination bite block and airway as a single unit, single unibody design, with the optional curved portion of the tongue depressor and optional insertion knob.

FIG. 10 is an embodiment of a bilateral bite block with tongue depressor between the left and right sides, with the optional curved portion of the tongue depressor and bilateral optional insertion knobs.

DETAILED DESCRIPTION

Figure 1:
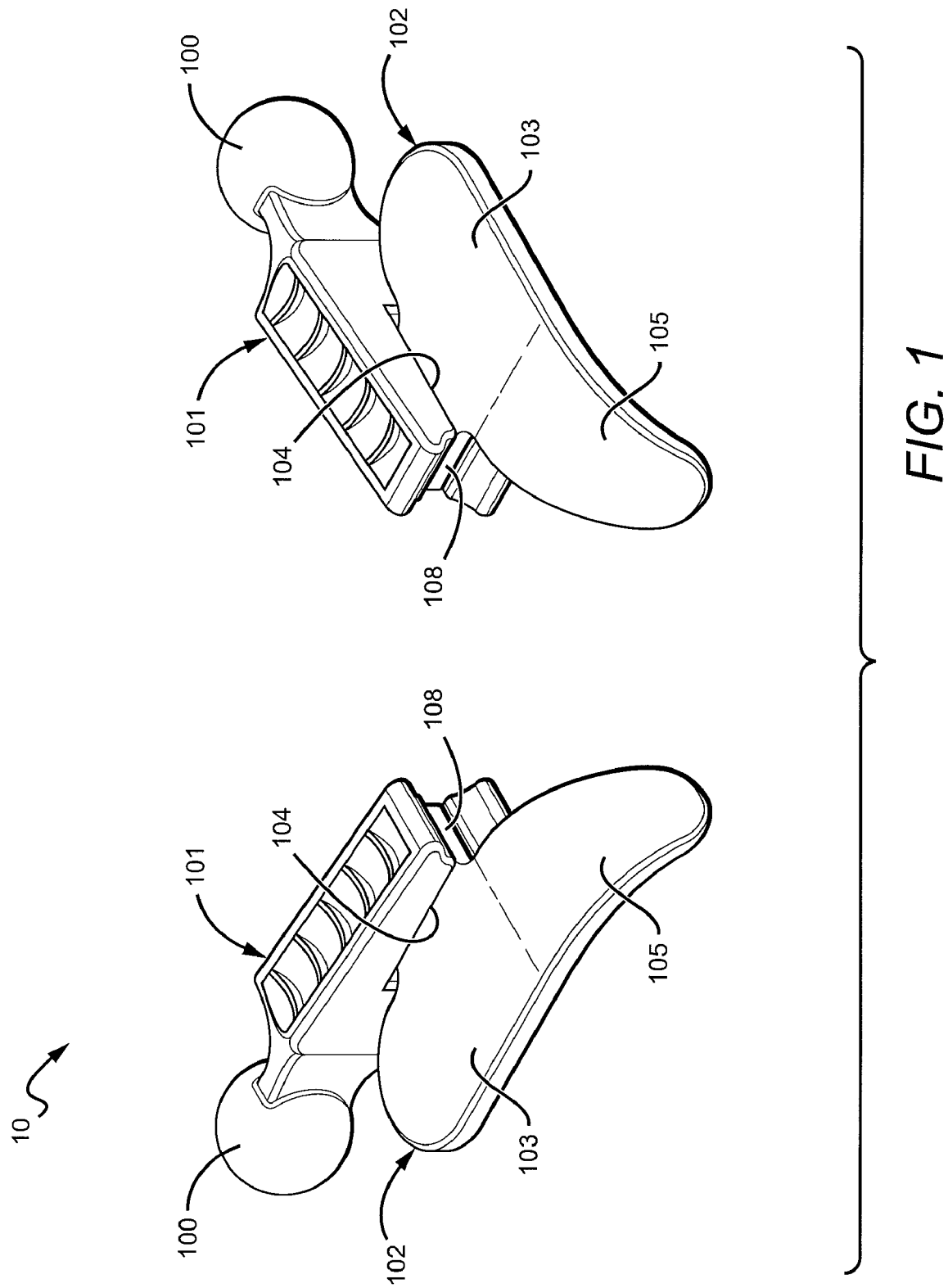
FIG. 1 is a perspective view of the present inventive subject matter in one embodiment as an assembly interference fit design.

In FIG. 1, a bite block 10 generally comprises a bite block component 101 and a tongue depressor component 102. The bite block component 101 is generally wedge shaped, and is preferably made of a compressible component, sized and shaped to be inserted between the upper and lower molars on either the right or left side of the mouth. The tongue depressor component is generally ramp-shaped, with an anterior flatter portion 103 that is inserted into an insertion point 104 in the side of the bite block, and an optional posterior curved portion 105 that retracts the tongue off of the posterior pharynx when in place. FIG. 1 also shows the mating element 108, which inserts into channel 204 of the bite block component. As used herein, wedge-shaped is any shape that has a largely triangular or trapezoidal shape, and ramp-shaped is any shape that has an inclined surface.

The wedge shaped bite block has a wide anterior portion that angles down to a narrower posterior portion in such dimensions that the teeth are kept sufficiently apart for endoscopic procedures and examination, insertion and maintenance of airway appliances or endoscopic examination devices. The angles and dimensions of the bite block are such that inserting the bite block between the upper and lower molars prevents clenching of teeth that can damage the weaker anterior teeth, particularly the incisors. Also, the dimensions can help prevent damage to soft tissues during clenching, particularly the tongue. In addition, the edges of the bite block component are preferably rounded to decrease the risk of soft tissue damage by preventing soft tissue from contacting a sharper, edged surface. As stated before, the bite block is preferably compressible to prevent damage to either soft tissue or the teeth due to grinding or other friction forces.

Figure 2:
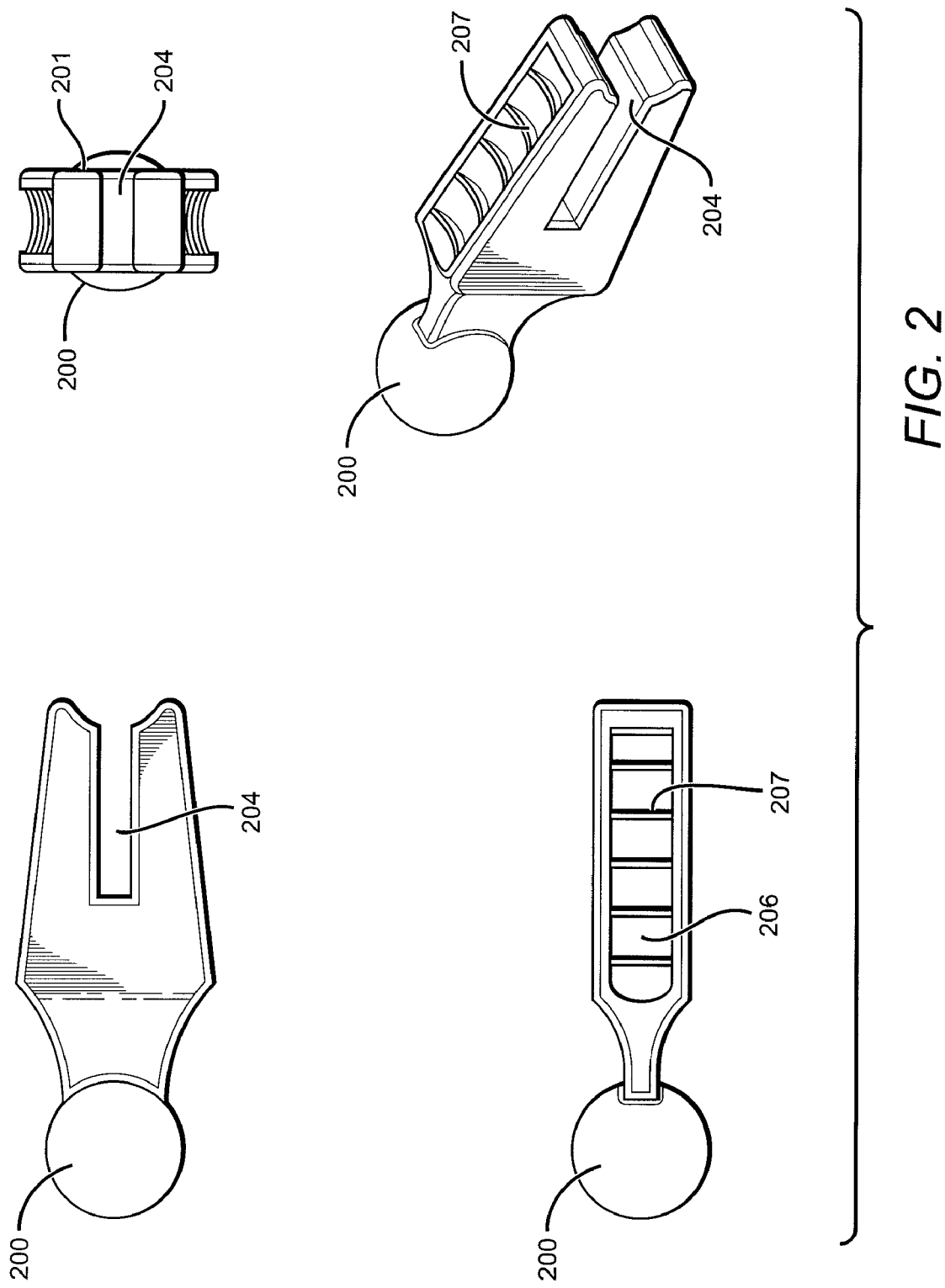
FIG. 2 is an embodiment of the bilateral bite block component in the left-seated manifestation of the assembly interference fit design of FIG. 1.

The dimensions of the bite block are preferably selected to prevent the jaw from being widely displaced into an anatomically uncomfortable position, as is the case with most bite blocks designed for dental practice. As shown in FIG. 2, bite block 201 could have depressions 206 for the upper and lower molars (not shown) to rest within. Also, the depressions could be preferably located at specified intervals where the molars normally or ideally rest to help to prevent displacement of the bite block by jaw movement. Each depression is preferably surrounded on all four sides by a low wall or ridge 207 to hold each tooth in place against the bite block, as well as to prevent teeth from sliding to either side and bite soft tissue, such as the tongue or the inside of the patient's cheek. In this embodiment bite block 201 has insert channel 204 to receive a lateral edge of the tongue depressor. While channel 204 is preferably situated medially in the bite block, the insert channel can be situated in any suitable location for coupling. This bite block could be inserted on either the left or right side of the mouth depending upon clinical indications and patient conditions.

Figure 5:
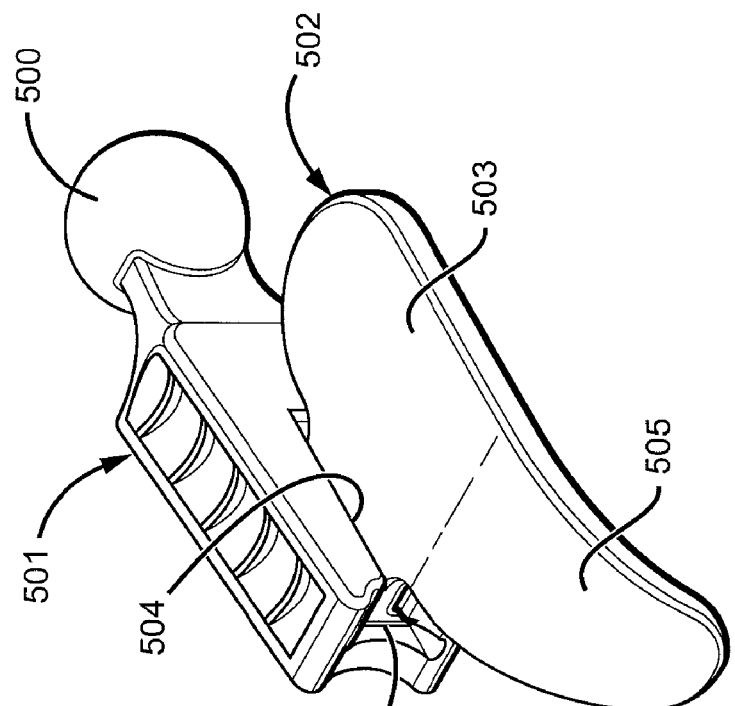
FIG. 5 is a perspective view of the present inventive subject matter in one embodiment as an assembly T-lock design.
Figure 5:
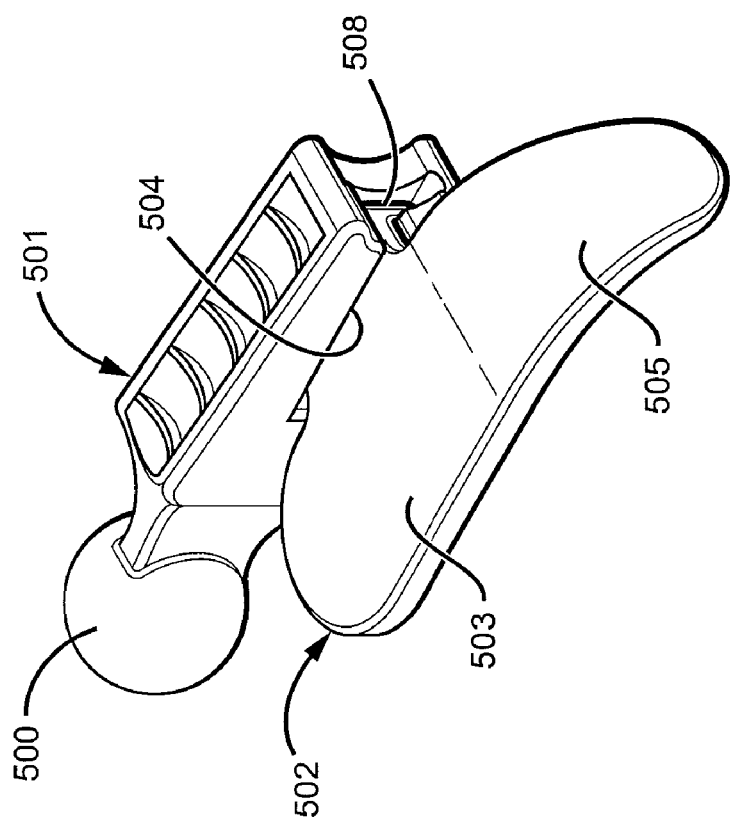
Figure 6:
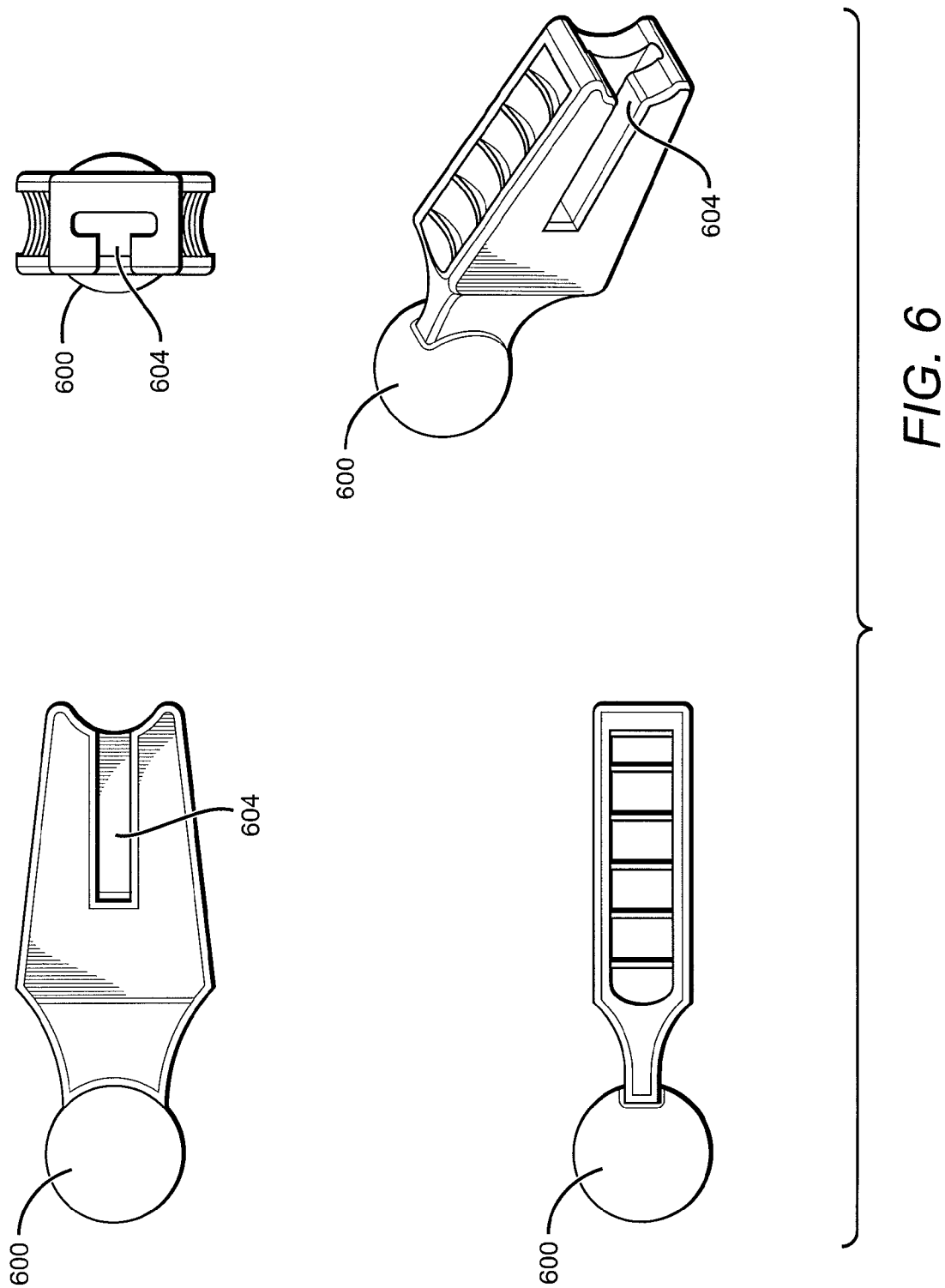
FIG. 6 is an embodiment of the bilateral bite block component of the assembly T-lock design of FIG. 5.

An optional insertion knob, seen in FIG. 1 as 100, FIG. 2 as 200, FIG. 5 as 500, FIG. 6 as 600, FIG. 9 as 900, and FIG. 10 as 1000 facilitates insertion and removal of the bite block between the molars on either the left or the right side of the patient's mouth, while enabling assisted or controlled-bag mask ventilation. While the knob can be shaped in any suitable fashion, the knob is preferably round-shaped, so that a user of the device can easily orient the device to any angle relative to the knob by rolling the knob within the user's thumb and forefinger. The insertion knob also provides protection to the healthcare provider from being bitten during insertion and removal of the device by providing a handy grip that extends outwardly from the anterior teeth.

The structural and functional variations of preferred bite blocks include the following: (1) an assembly interference fit design (FIGS. 1-4); (2) an assembly lock design (FIGS. 5-8); (3) a single unibody design (FIG. 9); and (4) a bilateral design (FIG. 10).

Figure 3:
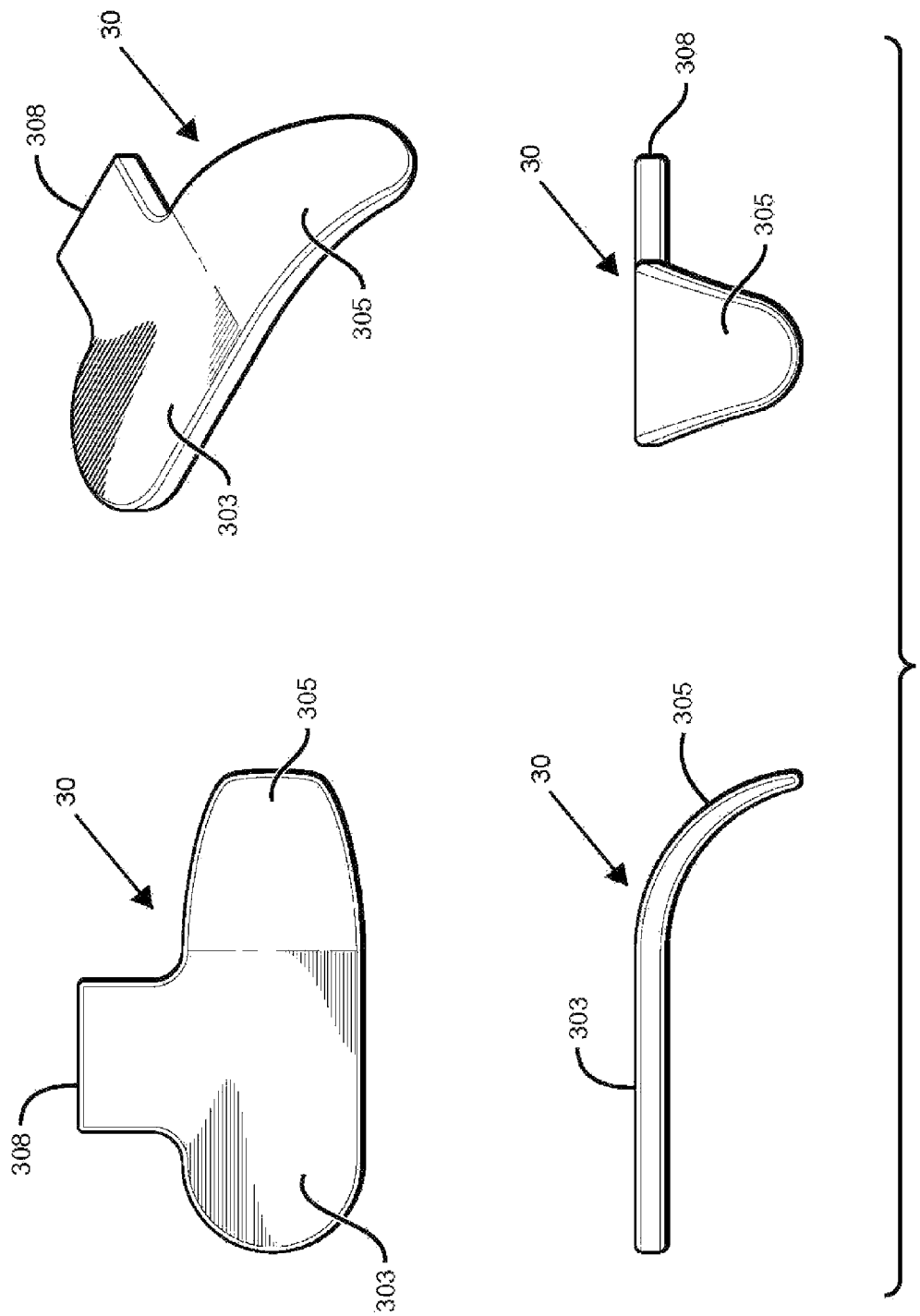
FIG. 3 is an embodiment of the tongue depressor component in the right-seated manifestation of the assembly interference fit design of FIG. 1.

The assembly interference fit design can have both a left and right form of the tongue depressor. FIG. 3 illustrates an exemplary right tongue depressor form 30, which is inserted into the bite block that separates the upper and lower molars on the right side of the mouth. Tongue depressor 30 has insertion edge 308, which can be inserted into channel 204 of the assembly interference fit design of FIG. 2. Edge 308 inserts into bite block 201, which separates the upper and lower molars of the right side of the mouth. Tongue depressor 30 also includes anterior portion 303 and posterior portion 305. Anterior portion 303 is the upper, anterior surface of the tongue depressor that holds the patient's tongue down while the bite block is in place and posterior portion 305 the lower, posterior surface that hooks back behind the tongue, retracting it off of the posterior pharynx, opening the airway and providing greater visualization of the posterior pharynx and airway structures during endoscopy. While the tongue depressor portion preferably has both an anterior and a posterior portion, a ramped posterior portion is not necessary in all embodiments.

Anterior portion 303 is shaped and dimensioned to prevent the front, anterior teeth, particularly the incisors, from accidentally biting into the tongue depressor. Preferably, the anterior surface 303 has a rounded edge, contouring to the shape and size of the user's tongue to rest comfortably on top of the surface. Posterior surface 305 is shaped and dimensioned to retract the tongue off of the posterior pharynx when in place.

As shown in FIG. 3, posterior surface 305 is preferably a curved ramp that contours to the shape of a tongue when at its lowest position, but can be shaped and dimensioned in any suitable manner to retract the tongue off of the posterior pharynx. Posterior surface 305 could be detachable from anterior surface 303, but the posterior surface 305 and the anterior surface 303 are preferably made from a single material. Since the tongue depressor is shaped and dimensioned to not come in contact with the patient's teeth, the tongue depressor could be made of a tougher, stronger, more resilient material than the bite block.

Figure 4:
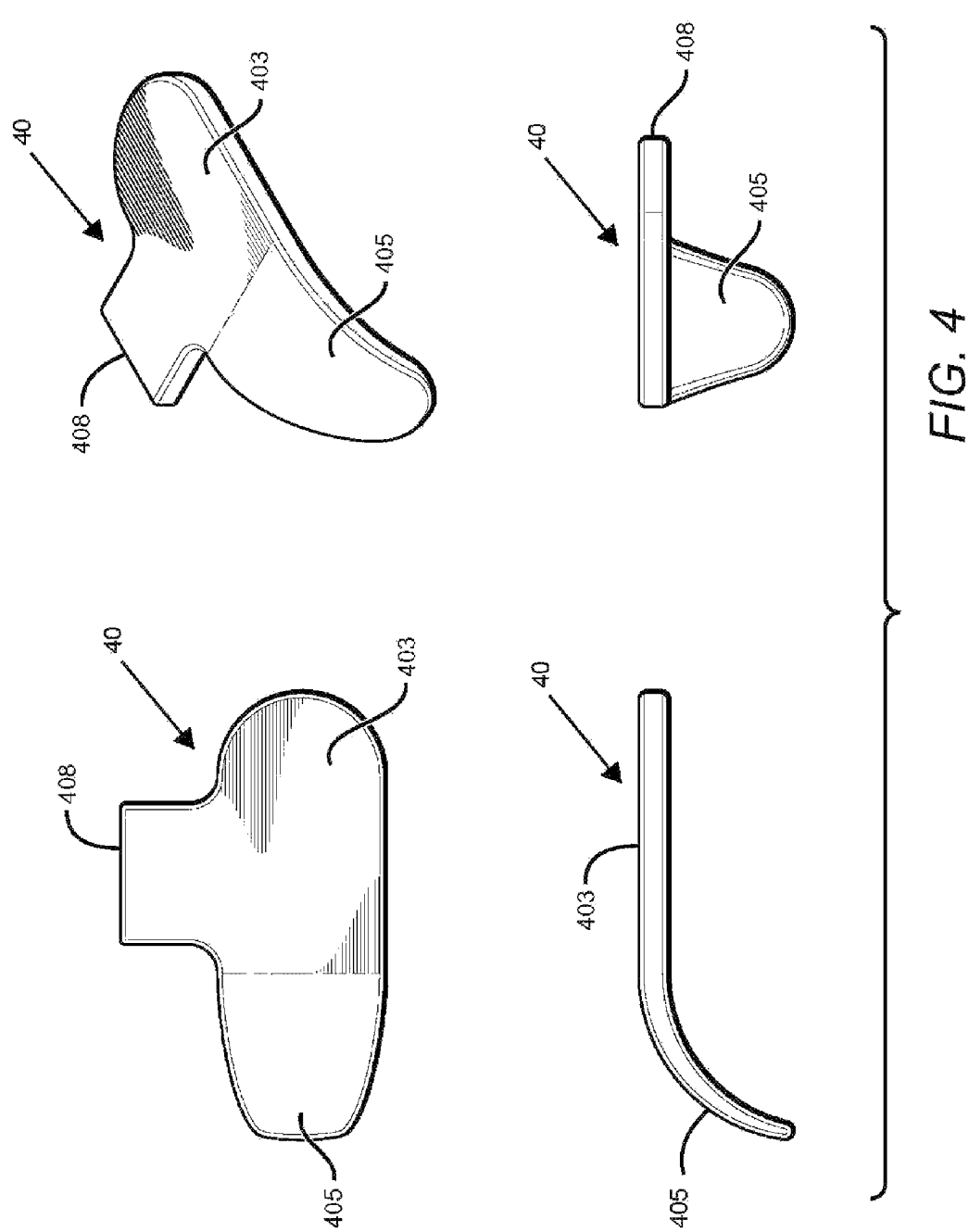
FIG. 4 is an embodiment of the tongue depressor component in the left-seated manifestation of the assembly interference fit design of FIG. 1.

FIG. 4 illustrates a left form tongue depressor 40 of a contemplated assembly interference fit design. The left form tongue depressor is inserted into the bite block, which separates the upper and lower molars of the left side of the mouth, and is a mirror image of tongue depressor 30. FIG. 4 shows the analogous components of the left form of the tongue depressor of the assembly interference fit design. Edge 408 is analogous to edge 308 in FIG. 3. Edge 408 can insert into the bite block at channel 204, which separates the upper and lower molars of the left side of the mouth. In the left sided version, portions 403 and 405 provide the same functions as portion 303 and 305 in the right-sided version.

FIG. 5 shows an exemplary assembly T lock design bite block 501 with tongue depressor 502, which differs from the assembly interference fit design bite block of FIG. 2 in the shape and dimensions of the insertion channel 504 and edge 508 for the tongue depressor component. A detailed view of the T-lock interference fit design is shown in FIG. 6 with central channel 604 and knob 600. Note that the bite block itself can be rotated to fit on either a patient's left side molars or the patient's right side molars. Analogous to the other embodiments, elements 503, 703, and 803 represent the anterior, flat portion of the tongue depressor, and elements 505, 705, and 805 represent the posterior, ramped portion of the tongue depressor.

Figure 7:
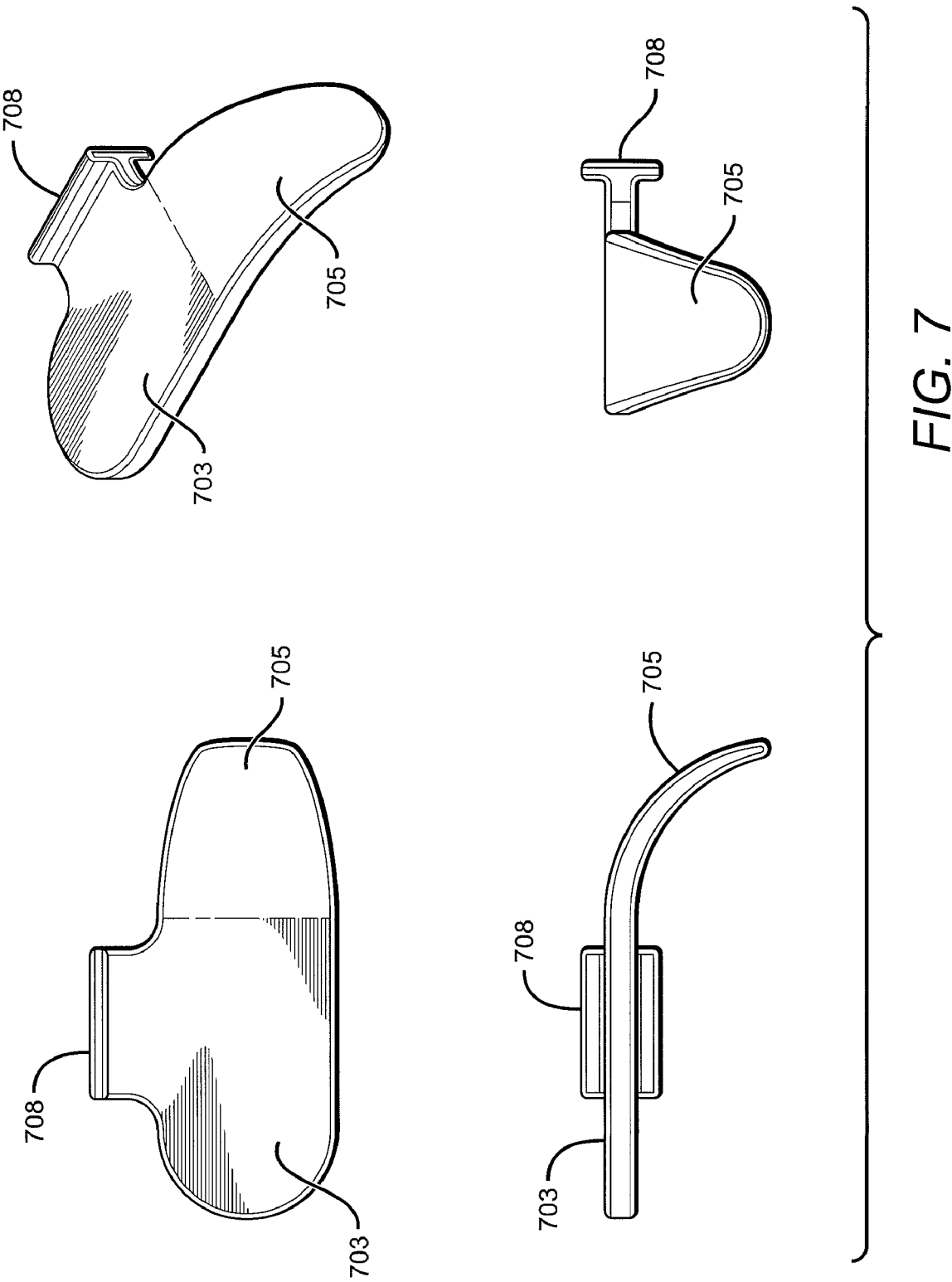
FIG. 7 is an embodiment of the right-seated tongue depressor component in the right-seated manifestation of the assembly T-lock design of FIG. 5.
Figure 8:
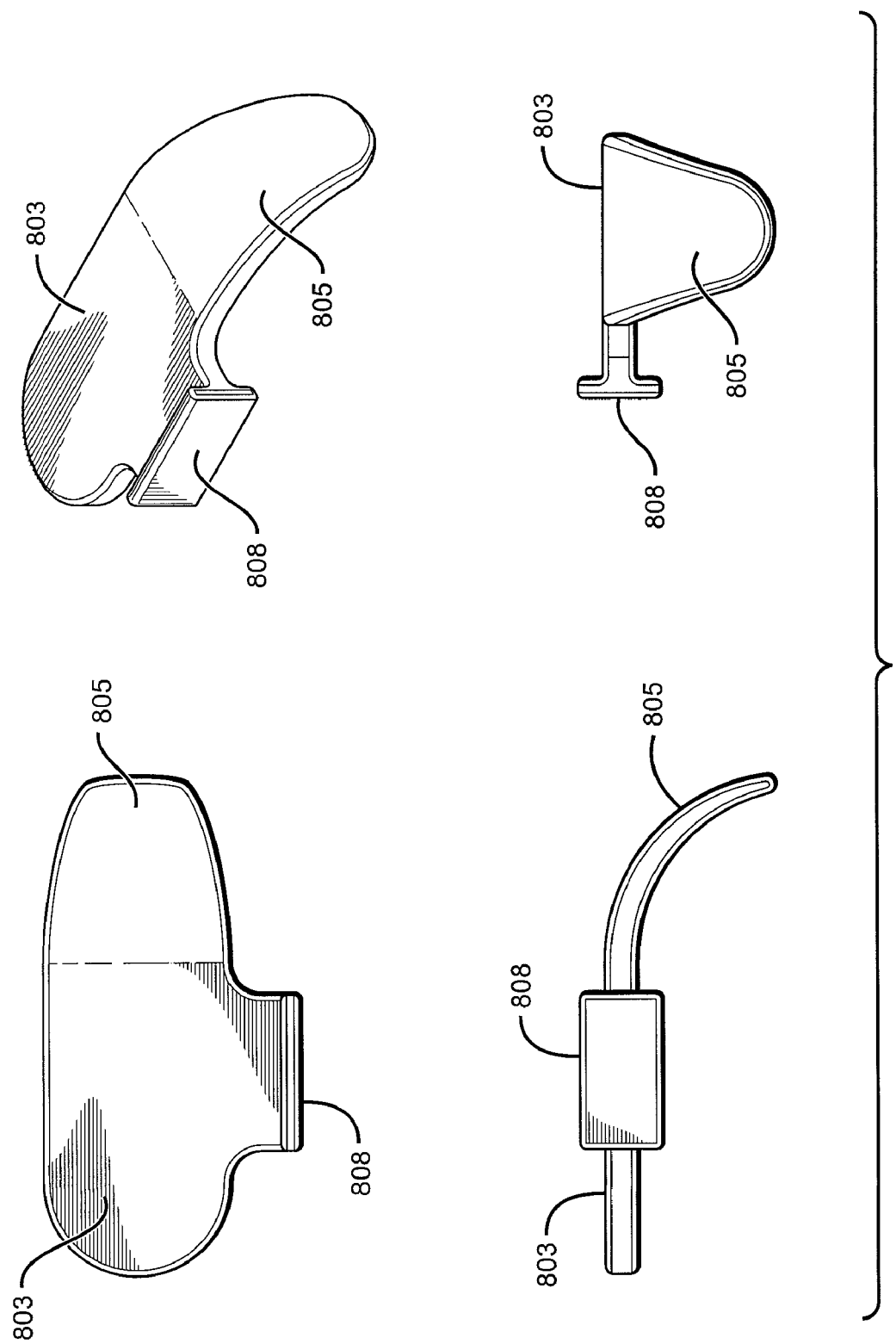
FIG. 8 is an embodiment of the right-seated tongue depressor component in the left-seated manifestation of the assembly T-lock design of FIG. 5.

The assembly T-lock design tongue depressor differs from the assembly interference fit design tongue depressor in the mating component with the bite block. FIGS. 7 and 8 show mating elements 708 and 808, respectively, which are T-shaped and designed for insertion into receiving channel 604 noted in FIG. 6 of the assembly T-lock bite block design. While a T-shaped design can be used to lock the tongue depressor to the bite block, other designs could be used without departing from the scope of the current inventive subject matter. For example, the mating elements could have indents that match detents in the receiving channel to help the tongue depressor snap into place, or the tongue depressor could rotate into a locking channel.

In FIG. 9, an embodiment of the single unibody design has a bite block 902 and tongue depressor/retractor 905 as a molded single piece without the capacity for separation of the two components. This embodiment obligates left and right laterality to the entire device. Element 900 describes the optional insertion knob. Tongue depressor 905 has a posterior curved portion of the tongue depressor, but of course the posterior portion of the tongue depressor could be shaped differently or could be eliminated altogether. One skilled in the art could also create a unibody design from the assembly interference fit design or the assembly T-shaped design by permanently coupling the tongue depressor with the bite block using a strong adhesive or glue.

While the single unibody design prevents the tongue depressor component from shifting or sliding during use, the single unibody design also restricts the bite block apparatus and mandates laterality to the entire device, whereas the assembly T-lock design and assembly interference fit design only mandate laterality to the tongue depressor component, and not to the bite block component.

FIG. 10 Shows an embodiment of the bilateral bite block design. Knobs 1000 are shown as being attached to both the right and left bite blocks, but could be placed only on one side of the mouth, or could be shaped in a different manner. The anterior portion 1003 of the tongue depressor can be inserted into bite blocks on either side, or could be permanently attached to the bite blocks. A ramped posterior portion could also be attached to the tongue depressor to help keep the air passage open.

In all of the preferred embodiments shown, the anterior edge of the tongue depressor component preferably does not extend as far forward as the anterior teeth. This prevents the tongue depressing portion of the device from conducting any significant forces against anterior teeth of the patient. A "significant force" is defined herein as a vertical or horizontal force greater than 25 lbs. that is applied to the anterior teeth.

All of these components can advantageously be manufactured by injection molding of suitable biologically inert, medical grade, latex free polymers as a reusable or disposable device. Biodegradable polymers with suitable physical characteristics can also be utilized as they become available. Devices can be scaled to different proportional dimensions to accommodate the differing airway sizes of patients of all ages and physical dimensions.

Operation of the Inventive Subject Matter

In both the assembly interference fit design and assembly T-lock design embodiments, the practitioner mates the bite block with the tongue depressor either before or after insertion into the patient. With the assembly interference fit design embodiment, the practitioner preferably inserts the tongue depressor into the bite block by sliding it either laterally or from the posterior aspect of the bite block depending upon the application. With the assembly T-lock design embodiment, the practitioner preferably inserts the tongue depressor component from the posterior aspect of the bite block and slides it forward until full mating is achieved. With the Single Unibody construction, no assembly is required for use.

In one aspect of the inventive subject matter, the bite block and tongue depressor can be assembled prior to insertion into a patient. The assembly interference fit design offers the option of assembly of the components either prior to or after insertion into the patient. While the assembly T-lock design may be assembled after insertion into the patient, the assembly T-lock design and the single unibody design are typically assembled before insertion into the patient.

Any of the proposed embodiments have the option of insertion by direct placement into the patient's mouth or the option of lateral rotation of the assembled components by either 90 or 180° and rotated into position as is the typical practice with the Guedel airway and its derivatives. In contrast with the Guedel airway and its derivatives, however, seating of the bite block between the molar teeth and/or posterior gums is crucial to the intended prevention of dental damage of the fragile anterior teeth. An embodiment of the Assembly Interference Fit Design is shown in FIG. 1. Both the right and left mounts are shown. Element 100, the insertion and removal knob, protrudes from the patient's mouth with sufficient clearance to allow bag-mask assisted or controlled ventilation. Element 104 shows the junction between the tongue depressor in the bite block. Element 108 shows the full insertion and mating of the tongue depressor with the bite block. Element 101 is the bite block itself, and element 102 is the tongue depressor/retractor. The bite block may be left in place after the tongue depressor is removed in order to prevent gagging as necessary while maintaining prevention of dental damage from emergence clenching. Thus provocation of the gag reflex by the tongue depressor can be avoided while leaving the bite block in place to prevent dental damage on emergence from anesthesia, sedation, or seizures.

As to a further discussion of the manner of usage and operation of the present inventive subject matter, the same should be apparent from the above description. Accordingly, no further discussion relating to the manner of usage and operation will be provided.

With respect to the above description then, it is to be realized that the optimum dimensional relationships for the parts of the inventive subject matter, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present inventive subject matter.

Thus, specific embodiments and applications of a combination bite block, tongue depressor/retractor and airway have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

The invention claimed is:

1. An apparatus for preventing emergence clenching dental trauma and maintaining an open airway in a patient, comprising: a molar receiving portion for a single side of a mouth; and a tongue depressing portion coupled medially to the molar receiving portion, having a posterior portion extending inferiorly towards a posterior end of a tongue of the patient to retract the tongue off of a posterior pharynx of the patient, wherein a length of the molar receiving portion is substantially parallel to a length of the tongue depressing portion and wherein the apparatus further comprising a knob coupled to an anterior portion of the molar receiving portion, and a taper between the anterior portion and the handle.

2. The apparatus of claim 1, wherein the tongue depressing portion has an anterior flattened portion.

3. The apparatus of claim 2, wherein the posterior portion has a posterior smoothly curved ramp.

4. The apparatus of claim 1, wherein the taper comprises a superior curve and an inferior curve.

5. The apparatus of claim 4, wherein the superior curve is asymmetrical with respect to the inferior curve.

6. The apparatus of claim 1, wherein the molar receiving portion is wedge shaped.

7. The apparatus of claim 1, wherein the molar receiving portion includes a slot that receives a lateral edge of the tongue depressing portion.

8. The apparatus of claim 1, wherein the molar receiving portion includes left and right slots with open recesses on opposing sides of the molar receiving portion, respectively, sized and dimensioned to receive right and left ones of the tongue depressing portion, respectively.

9. The apparatus of claim 1, wherein the molar receiving portion and the tongue depressing portion are permanently coupled together.

10. The apparatus of claim 1, wherein the molar receiving portion and the tongue depressing portion are molded from one single unit.

11. The apparatus of claim 1, wherein the knob is a substantially spherical.

* * * * *